United States Patent [19]

Kreuzer et al.

[11] Patent Number: 4,678,283

[45] Date of Patent: Jul. 7, 1987

[54] TRIALKANOYLOXYSILANES

[75] Inventors: Franz-Heinrich Kreuzer, Martinsried; Rudolf Eidenschink, Münster; Georg Weber, Erzhausen, all of Fed. Rep. of Germany

[73] Assignee: Merck Patent Gesellschaft mit Beschrankter Haftung, Darmstadt, Fed. Rep. of Germany

[21] Appl. No.: 647,210

[22] Filed: Sep. 4, 1984

[30] Foreign Application Priority Data

Sep. 1, 1983 [DE] Fed. Rep. of Germany ....... 3331515

[51] Int. Cl.$^4$ .................. G02F 1/13; C09K 19/56; C09K 19/54; C07F 7/04
[52] U.S. Cl. ................ 350/340; 252/299.4; 252/299.5; 556/416; 556/442; 556/445; 556/448; 428/1
[58] Field of Search ............... 556/416, 442, 445, 448; 252/299.4, 299.6, 299.63, 299.66, 299.01, 299.5; 350/339 R, 340; 428/1

[56] References Cited

U.S. PATENT DOCUMENTS

| | | | |
|---|---|---|---|
| 4,176,130 | 11/1979 | John et al. ........................ | 556/442 |
| 4,308,212 | 12/1981 | Takamizawa et al. ............ | 556/442 |
| 4,316,041 | 2/1982 | Totten et al. ..................... | 252/299.4 |
| 4,358,391 | 10/1980 | Finkelmann et al. ............ | 252/299.4 |
| 4,388,453 | 6/1983 | Finkelmann et al. ............ | 252/299.4 |
| 4,410,570 | 10/1983 | Kreuzer et al. .................. | 252/299.6 |
| 4,469,408 | 9/1984 | Kruger et al. .................... | 252/299.4 |
| 4,492,482 | 1/1985 | Totten et al. ..................... | 252/299.4 |

FOREIGN PATENT DOCUMENTS

54/24831  2/1979  Japan ............................... 252/299.4

OTHER PUBLICATIONS

Cornubert et al., Bull. Soc. Chim., 4, 23 (1928), 74.
Waser et al., Helv. Chim. ACTA, 12 (1929), 418.
Demus, Flussige Kristalle in Tabellen, vol. II (1984).

*Primary Examiner*—Teddy S. Gron
*Assistant Examiner*—J. E. Thomas
*Attorney, Agent, or Firm*—Millen & White

[57] ABSTRACT

Trialkanoyloxysilanes of the formula I

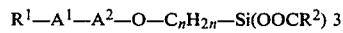

$$R^1-A^1-A^2-O-C_nH_{2n}-Si(OOCR^2)_3 \quad \text{I}$$

wherein $R^1$ is H or an alkyl group of 1-10 c atoms, wherein one or two non-adjacent $CH_2$ groups may also be replaced by oxygen atoms, or is F, Cl, Br or CN, $R^2$ is an alkyl group of 1-5 atoms, $A^1$ and $A^2$ are each 1,4-phenylene or 1,4-cyclohexylene groups and n is 2, 3, 4, 5 or 6, can be used for generating a homeotropic orientation of liquid-crystalline phases on surfaces.

19 Claims, No Drawings

TRIALKANOYLOXYSILANES

BACKGROUND OF THE INVENTION

Hitherto the generation a homogeneous and stable homeotropic orientation of liquid-crystalline phases was technologically fairly difficult. For instance, the liquid-crystalline phase used was doped with surface-active substances, such as lecithins, long-chain aliphatic amines, quaternary ammonium or phosphonium salts or carboxylatochromium complexes (Appl. Phys. Lett. 27,268 (1975)). It was also customary to coat glass surfaces with said substances before introducing the liquid-crystalline phase. However, the uniformity and stability of the resulting homeotrophic orientation of liquid-crystalline phases leave something to be desired.

SUMMARY OF THE INVENTION

Accordingly, it is an object of the invention to make possible a better, in particular more uniform and more stable homeotropic orientation of liquid-crystalline phases on surfaces.

Upon further study of the specification and appended claims, further objects and advantages of this invention will become apparent to those skilled in the art.

These objects have been achieved by this invention by providing new trialkanoyloxysilanes of the formula I $$R^1 - A^1 - A^2 - O - C_nH_{2n} - Si(OOCR^2)_3 \qquad (I)$$

wherein $R^1$ is H or an alkyl group of 1-10 C atoms wherein one or two non-adjacent $CH_2$ groups may also be replaced by oxygen atoms, or is F, Cl, Br or CN, $R^2$ is an alkyl group of 1-5 C atoms, $A^1$ and $A^2$ are each independently 1,4-phenylene 1,4-cyclohexylene groups 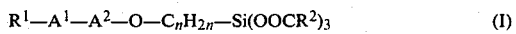 and n is 2, 3, 4, 5 or 6.

The compounds of the formula I are highly suitable for achieving homeotropic alignment of liquid-crystalline phases on surfaces, for example, glass plates which may also be coated, and are used in the manufacture of visual electronic display elements. Liquid-crystalline phases orientated in such a way can be affected by an external electric field in their alignment owing to their negative dielectric anisotrophy. They are suitable for use in displays which work on the principle of the deformation of oriented phases (Appl. Phys. Lett. 19, 391 (1971), the principle of dynamic scattering (Proc. IEEE 56, 1162 (1968) or the guest-host-principle (Mol. Cryst. Liq. Cryst. 64, 19 (1981).

The invention thus provides the compounds of the formula I and a process for their preparation which is characterized in that a trichlorosilane of the formula II $$R^1 - A^1 - A^2 - O - C_nH_{2n} - SiCl_3 \qquad II$$

wherein $R^1$, $A^1$, $A^2$ and n are as defined above, is reacted with an acid anhydride of the formula III $$(R^2CO)_2O \qquad III$$

wherein $R^2$ is as defined above.

The invention also provides the use of the compounds of the formula I as components of liquid-crystalline dielectric media for visual electronic display elements and their use for generating a homeotropic orientation of liquid-crystalline phases on surfaces. The invention further provides liquid-crystalline dielectric media containing at least one compound of the formula I, as well as visual electronic display elements which contain such dielectric media and/or surfaces which have been treated with a compound of the formula I.

DETAILED DISCUSSION

Heretofore and hereinafter $R^1$, $R^2$, $A^1$, $A^2$ and n are as defined above, unless expressly stated otherwise.

According to the definition of the $A^1$ and $A^2$ groups, the compounds of the formula I include those of formulae Ia to Id:

$$R^1-Phe-Phe-O-C_nH_{2n}-Si(OOCR^2)_3 \qquad Ia$$
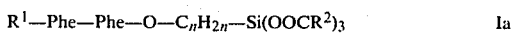

$$R^1-Cy-Phe-O-C_nH_{2n}-Si(OOCR^2)_3 \qquad Ib$$
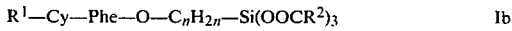

$$R^1-Phe-Cy-O-C_nH_{2n}-Si(OOCR^2)_3 \qquad Ic$$

$$R^1-Cy-Cy-O-C_nH_{2n}-Si(OOCR^2)_3 \qquad Id.$$

In these formulae, Phe is 1,4-phenylene and Cy is 1,4-cyclohexylene. Compounds of the formulae Ib and Id are preferred.

In the compounds of the formulae mentioned heretofore and hereinafter, $R^1$ preferably is alkyl or is alkoxy (in particular when this radical is attached to a Phe group) or a different oxaalkyl group.

The parameter n is preferably 3. The radical $C_nH_{2n}$ is preferably straight-chained and is accordingly in particular $-(CH_2)_3-$ or in particular $-(CH_2)_2-$, $-(CH_2)_4-$, $-(CH_2)_5-$ or $-(CH_2)_6-$.

In the compounds of the formulae mentioned heretofore or hereinafter, the alkyl radicals can be straight-chain or branched. Preferably they are straight-chained, have 1, 2, 3, 4 or 5, in the case of $R^1$ even 6 or 7C atoms, and are accordingly preferably methyl, ethyl, propyl, butyl, pentyl, or in the case of $R^1$ also hexyl or heptyl.  $R^1$ can also be an alkyl group wherein one ("alkoxy" or "oxaalkyl") or 2 ("alkoxyalkoxy" or "dioxaalkyl") non adjacent $CH_2$ groups may be replaced by 0 atoms, preferably methoxy, ethoxy, propoxy, butoxy, pentoxy, hexoxy, heptoxy, 2-oxapropyl (=methoxymethyl), 2-(=ethoxymethyl) or 3-oxabutyl (=3-methoxyethyl), 2-, 3- or 4-oxapentyl, 2-, 3-, 4- or 5-oxahexyl or 2-, 3-, 4-, 5- or 6-oxaheptyl.

$R^1$ can also be, for example, octyl, nonyl, decyl, octoxy, nonoxy, decoxy, 2-, 3-, 4-, 5-, 6- or 7-oxaoctyl, 2-, 3-, 4-, 5-, 6-, 7- or 8-oxanonyl, 2-, 3-, 4-, 5-, 6-, 7-, 8- or 9-oxadecyl, 1,3-dioxabutyl (=methoxymethoxy), 1,3-,  1,4- or 2,4-dioxapentyl, 1,3-, 1,4-, 1,5-, 2,4-, 2,5-, 2,6-, 3,5-, 3,6- or 4,6 dioxaheptyl. $R^1$ is preferably also F, Cl, Br or CN.

Compounds of the formulae I as well as Ia to Id having branched $R^1$ and/or $R^2$ radicals can occasionally be of importance—because of superior solubility in the customary liquid-crystalline base materials—and can be dopants if they are optically active. Branched groups of this type generally contain no more than one branch in the chain. Preferred branched $R^1$ and $R^2$ radicals are isopropyl, 2-butyl (=1-methylpropyl), isobutyl (=2-methylpropyl), 2-methylbutyl and isopentyl (=3-methyl-butyl), $R^1$ can also be 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-menthylpentoxy, 1-methylhexoxy, 1-methylheptoxy, 2-ethylhexoxy, 2-oxa-3-methylbutyl or 3-oxa-4-methylpentyl.

In particular, the radical $R^2$ is preferably a methyl group.

If the $A^1$ and/or $A^2$ groups are cyclohexylene groups which are disubstituted in the 1- and 4-positions, the substituents can be in the cis- or trans-position. Compounds with trans-configuration are preferred.

Compounds of the formula I having optically active C atoms encompass not only the racemates but also the corresponding optically active enantiomers as well as their mixtures.

The compounds of the formula I can be prepared by methods known per se, as described in the literature (for example in standard works such as Houben-Weyl, Methoden der Organischen Chemie (methods of Organic Chemistry), published by Georg Thieme, Stuttgart), under reaction conditions known and suitable for said reactions. These reactions can also be carried out using variants known per se but not specifically mentioned here.

The starting materials, in particular those of the formula II, can, if desired, also be formed in situ in the sense that they are not isolated from the reaction mixture but are immediately further reacted to the compounds of the formula I.

The trichlorsilanes of the formula II are new. They can be prepared, for example, by reacting an unsaturated ether of the formula IV

$$R^1-A^1-A^2-O-C_nH_{2n-1} \qquad \text{IV}$$

with trichlorosilane.

The ethers of the formula IV can in turn be prepared by alkenylating hydroxy compounds of the formula V

$$R^1-A^1-A^2-OH \qquad \text{V}$$

with an appropriate alkenyl halide of the formula $C_nH_{2n-1}Cl$ or $C_nH_{2n-1}Br$. All starting materials are known and/or readily prepared from known starting materials.

The addition of trichlorosilane onto the unsaturated ethers of the formula IV is preferably accomplished at temperatures between about 0° and about 100°, preferably at the boil, in the presence of an inert solvent, for example a halogenated hydrocarbon, such as dichloromethane. Trichlorosilane is advantageously used in excess. And it is an advantage to add a noble metal catalyst, for example a solution of $H_2PtCl_6$ in isopropanol. The resulting product of the formula II is preferably not purified but is reacted in the crude state with the acid anhydride of the formula III, preferably no additional solvent being added but an excess of anhydride being used as the solvent. The reaction temperatures are advantageously between 50° and about 200°, preferably between 120° and 160°.

The compounds of the formula I can be immediately used for coating the surfaces to be treated. Suitable surfaces for coating are in particular oxidic surfaces, for example, those of metal oxides, semimetal oxides or non-metal oxides, but especially glass surfaces.

The coating is preferably applied by wetting the previously cleaned surfaces with an approximately 0.1 to 1% solution of a compound of the formula I in an inert solvent, for example a halogenated hydrocarbon such as dichloromethane, evaporating the solvent, exposing the surface to a humid atmosphere—in order to hydrolyze the ester bonds—and then briefly heating the surface, the result being a thin film of high molecular weight hydrolysis products.

However, one or more compounds of the formula I can be used as dopants added to liquid-crystalline dielectric media in amounts of about 0.01 to 1%, preferably about 0.05 to 0.5%.

The dielectric media according to the invention consist of 2 to 15, preferably 3 to 12, components among which is at least one compound of the formula I. The other components are preferably selected from among the nematic or nematogenic substances, in particular the known substances, of the classes of azoxybenzenbes, benzylidene-anilines, biphenyls, terphenyls, phenyl or cyclohexyl benzoates, phenyl or cyclohexyl cyclohexanecarboxylates, phenylcyclohexanes, cyclohexylbiphenyls, cyclohexylcyclohexanes, cyclohexylnaphtalenes, 1,4-biscyclohexylbenzenes, 4,4'-biscyclohexylbiphenyls, phenylpyrimidines, cyclohexylpyrimidines, phenyldioxanes, cyclohexyldioxanes, optionally halogenated stilbenes, benzyl phenyl ethers, tolanes and substituted cinnamic acids.

The most important potential compounds for use as components of such liquid-crystalline dielectric media can be characterized by the formula VI

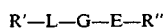
$$R'-L-G-E-R'' \qquad \text{VI}$$

wherein L and E are each a carbocyclic or heterocyclic ring system selected from the group comprising 1,4-disubstituted benzene and cyclohexane rings, 4,4'-disubstituted biphenyl, phenylcyclohexane and cyclohexylcyclohexane systems, 2,5-disubstituted pyrimidine and 1,3-dioxane rings, 2,6-disubstituted naphthalene, dihydronaphthalene, tetrahydronaphthalene, quinazoline and tetrahydroquinazoline,

| G is | —CH=CH— | —N(O)=N— |
|---|---|---|
| | —CH=CY— | —CH=N(O)— |
| | —C≡C— | —CH$_2$—CH$_2$— |
| | —CO—O— | —CH$_2$—O— |
| | —CO—S— | —CH$_2$—S— |
| | —CH=N— | —COO—Phe—COO— | or C—C single bond, Y is halogen, preferably chlorine, or —CN, and R' and R'' are each alkyl, alkoxy, alkanoyloxy or alkoxycarbonyloxy of up to 18, preferably up to 8, carbon atoms, or one of these radicals is also CN, NC, $NO_2$, $CF_3$, F, Cl or Br.

In most of these compounds, R' and R'' are different from each other, one of these radicals usually being an alkyl or alkoxy group. However, different variants of the proposed substituents are also customary. Many such substances or mixtures thereof are commercially available.

The dielectric media according to the invention are prepared in conventional manner per se. The components are generally dissolved in one another, preferably at elevated temperatures.

By means of suitable additives the liquid-crystalline dielectric media according to the invention can be modified in such a way that they can be used in any type of liquid crystal display elements disclosed to date.

The person skilled in the art is familiar with such additives, which are described in detail in the literature. For example, conducting salts, preferably ethyldimethyldodecylammonium 4-hexyloxybenzoate, tetrabutylammonium tetraphenylboronate or complex salts of crown ethers (cf. for example I. Haller et al., Mol. Cryst. Liq. Cryst. Volume 24, pages 249–258 (1973)) can be added to improve the conductivity, dichroic dyestuffs can be added to prepare colored guest-host systems, or substances can be added to change the dielectric anisotropy, the viscosity and/or the orientation of the nematic phases. Such substances are described, for example, in German Offenlegungsschriften Nos. 2,209,127, 2,240,864, 2,321,632, 2,338,281, 2,450,088, 2,637,430, 2,853,728 and 2,902,177.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following examples and in the preceding text, all temperatures are set forth uncorrected in degrees Celsius and all parts and percentages are by weight, unless otherwise indicated.

In the examples, m.p. is the melting point and c.p. is the clear point of a liquid crystal substance.

PREPARATION EXAMPLE 26.8 g of $HSiCl_3$ and then 0.5 ml of an 0.05 M solution of $H_2PtCl_6$ in isopropanol are added to a solution of 32.4 g of 3-(p-trans-4-propylcyolohexylphenoxy)-propene (m.p. 25°–28°; obtainable by reacting Na p-trans-4-propylcyclohexylphenolate with allyl bromide) in 60 ml of $CH_2Cl_2$. After two days at the boil the excess $HSiCl_3$ is distilled off. The resulting crude 1-trichlorosilyl-3-(p-trans-4-propylcyclohexylphenoxy)-propane is boiled for 5 hours with 76.8 g of acetic anhydride. This distilling-off of the excess acetic anhydride gives 1-triacetoxysilyl-3-(p-trans-4-propylcyclohexylphenoxy)-propane; m.p. 36°, c.p. 65°.

The following compounds are obtained analogously from the corresponding anhydrides:

1-Tripropionyloxysilyl-3-(p-trans-4-propylcyclohexylphenoxy)-propane
1-Tripropionyloxysilyl-3-(p-trans-4-propylcyclohexylphenoxy)-propane
1-Triisobutyryloxysilyl-3-(p-trans-4-propylcyclohexylphenoxy)-propane
1-Trivaleryloxysilyl-3-(p-trans-4-propylcyclohexylphenoxy)-propane
1-Tricapronyloxysilyl-3-(p-trans-4-propylcyclohexylphenoxy)-propane
1-Triacetoxysilyl-3-p-cyclohexylphenoxy-propane
1-Triacetoxysilyl-3-(p-trans-4-methylcyclohexylphenoxy)-propane
1-Triacetoxysilyl-3-(p-trans-4-ethylcyclohexylphenoxy)-propane
1-Triacetoxysilyl-3-(p-trans-4-butylcyclohexylphenoxy)-propane
1-Triacetoxysilyl-3-(p-trans-4-isobutylcyclohexylphenoxy)-propane
1-Triacetoxysilyl-3-(p-trans-4-sec.-butylcyclohexylphenoxy)-propane
1-Triacetoxysilyl-3-(p-trans-4-pentylcyclohexylphenoxy)-propane
1-Triacetoxysilyl-3-(p-trans-4-hexylcyclohexylphenoxy)-propane
1-Triacetoxysilyl-3-(p-trans-4-heptylcyclohexylphenoxy)-propane
1-Triacetoxysilyl-3-(p-trans-4-octylcyclohexylphenoxy)-propane
1-Triacetoxysilyl-3-(p-trans-4-nonylcyclohexylphenoxy)-propane
1-Triacetoxysilyl-3-(p-trans-4-decylcyclohexylphenoxy)-propane
1-Triacetoxysilyl-3-p-biphenylyloxy-propane
1-Triacetoxysilyl-3-(4'-methyl-biphenylyl-4-oxy)-propane
1-Triacetoxysilyl-3-(4'-ethyl-biphenylyl-4-oxy)-propane
1-Triacetoxysilyl-3-(4'-propyl-biphenylyl-4-oxy)-propane
1-Triacetoxysilyl-3-(4'-butyl-biphenylyl-4-oxy)-propane
1-Triacetoxysilyl-3-(4'-pentyl-biphenylyl-4-oxy)-propane
1-Triacetoxysilyl-3-(4'-hexyl-biphenylyl-4-oxy)-propane
1-Triacetoxysilyl-3-(4'-heptyl-biphenylyl-4-oxy)-propane
1-Triacetoxysilyl-3-(4'-octyl-biphenylyl-4-oxy)-propane
1-Triacetoxysilyl-3-(4'-nonyl-biphenylyl-4-oxy)-propane
1-Triacetoxysilyl-3-(4'-decyl-biphenylyl-4-oxy)-propane
1-Triacetoxysilyl-3-(4'-methoxy-biphenylyl-4-oxy)-propane
1-Triacetoxysilyl-3-(4'-ethoxy-biphenylyl-4-oxy)-propane
1-Triacetoxysilyl-3-(4'-propoxy-biphenylyl-4-oxy)-propane
1-Triacetoxysilyl-3-(4'-butoxy-biphenylyl-4-oxy)-propane
1-Triacetoxysilyl-3-(4'-pentoxy-biphenylyl-4-oxy)-propane
1-TriacetoxysiLyl-3-(4'-hexoxy-biphenylyl-4-oxy)-propane
1-Triacetoxysilyl-3-(4'-heptoxy-biphenylyl-4-oxy)-propane
1-Triacetoxysilyl-3-(4'-methoxymethyl-biphenylyl-4-oxy)-propane
1-Triacetoxysilyl-3-(4'-methoxymethoxy-biphenylyl-4-oxy)-propane
1-Triacetoxysilyl-3-(4'-fluoro-biphenylyl-4-oxy)-propane
1-Triacetoxysilyl-3-(4'-chloro-biphenylyl-4-oxy)-propane
1-Triacetoxysilyl-3-(4'-bromo-biphenylyl-4-oxy)-propane
1-Triacetoxysilyl-3-(4'-cyano-biphenylyl-4-oxy)-propane
1-Triacetoxysilyl-3-(trans-4-phenylcyclohexoxy)-propane
1-Triacetoxysilyl-3-(trans-4-p-tolylcyclohexoxy)-propane
1-Triacetoxysilyl-3-(trans-4-p-ethylphenylcyclohexoxy)-propane
1-Triacetoxysilyl-3-(trans-4-p-propylphenylcyclohexoxy)-propane
1-Triacetoxysilyl-3-(trans-4-p-butylphenylcyclohexoxy)-propane
1-Triacetoxysilyl-3-(trans-4-p-pentylphenylcyclohexoxy)-propane
1-Triacetoxysilyl-3-(trans-4-p-hexylphenylcyclohexoxy)-propane
1-Triacetoxysilyl-3-(trans-4-p-heptylphenylcyclohexoxy)-propane
1-Triacetoxysilyl-3-(trans-4-p-methoxyphenylcyclohexoxy)-propane
1-Triacetoxysilyl-3-(trans-4-p-ethoxyphenylcyclohexoxy)-propane
1-Triacetoxysilyl-3-(trans-4-p-propoxyphenylcyclohexoxy)-propane 1-Triacetoxysilyl-3-(trans-4-p-butoxyphenylcyclohexoxy)-propane
1-Triacetoxysilyl-3-(trans-4-p-pentoxyphenylcyclohexoxy)-propane
1-Triacetoxysilyl-3-(trans-4-p-fluorophenylcyclohexoxy)-propane
1-Triacetoxysilyl-3-(trans-4-p-chlorophenylcyclohexoxy)-propane
1-Triacetoxysilyl-3-(trans-4-p-bromophenylcyclohexoxy)-propane
1-Triacetoxysilyl-3-(trans-4-p-cyanophenylcyclohexoxy)-propane
1-Triacetoxysilyl-3-(trans-4-(trans-4-propylcyclohexyl)cyclohexoxy)-propane
1-Triacetoxysilyl-3-(trans-4-(trans-4-butylcyclohexyl)-cyclohexoxy)-propane
1-Triacetoxysilyl-3-(trans-4-(trans-4-pentylcyclohexyl)-cyclohexoxy)-propane
1-Triacetoxysilyl-3-(trans-4-(trans-4-hexylcyclohexyl)-cyclohexoxy)-propane
1-Triacetoxysilyl-3-(trans-4-(trans-4-heptylcyclohexyl)-cyclohexoxy)-propane
1-Triacetoxysilyl-2-(p-trans-4-propylcyclohexyl-phenoxy)-ethane
1-Triacetoxysilyl-4-(p-trans-4-propylcyclohexyl-phenoxy)-butane
1-Triacetoxysilyl-5-(p-trans-4-propylcyclohexyl-phenoxy)-pentane
1-Triacetoxysilyl-6-(p-trans-4-propylcyclohexyl-phenoxy)-hexane
1-Triacetoxysilyl-2-methyl-3-(p-trans-4-propylcyclohexyl)-phenoxy)-propane.

FORMULATION EXAMPLE (DIELECTRIC MEDIUM)

A mixture of
54% of p-trans-4-propylcyclohexylphenyl butyrate,
26% of trans-4-propylcyclohexyl p-trans-4-butylcyclohexylbenzoate,
19.9% of trans-4-propylcyclohexyl p-trans-4-propylcyclohexylbenzoate,
0.1% of 1-triacetoxysilyl-3-(p-trans-4-propylcyclohexylphenoxy)-propane
has a c.p. of 80°

USE EXAMPLE: COATING OF GLASS SURFACES

The pieces of glass, which have been carefully cleaned in 1,1,2-trichloroethane vapor, are wetted with an 0.5% solution of 1-triacetoxysilyl-3-(p-trans-4-propylcyclohexylphenoxy)-propane in $CH_2Cl_2$ and, when the solvent has evaporated, are transferred into a saturated humid atmosphere at room temperature. After 10 minutes the glass surfaces are heated at 120° for 5 minutes and are then allowed to cool down.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:
1. A trialkanoyloxysilane of the formula

$$R^1-A^1-A^2-O-C_nH_{2n}-Si(OOCR^2)_3$$

wherein $R^1$ is H, alkyl of 1-10 C atoms, alkyl of 1-10 C atoms wherein one or two non-adjacent $CH_2$ groups are replaced by oxygen atoms, F, Cl, Br or CN, $R^2$ is alkyl of 1-5 C atoms; $A^1$ and $A^2$ are independently each 1,4-phenylene (Phe) or 1,4-cyclohexylene (Cy) and n is 2, 3, 4, or 6.

2. 1-Triacetoxysilyl-3-(p-trans-4-propylcyclohexylphenoxy)-propane, a compound of claim 1.
3. A compound of claim 1 of the formula $$R^1-Phe-Phe-O-C_nH_{2n}-Si(OOCR^2)_3.$$

4. A compound of claim 1 of the formula $$R^1-Cy-Phe-O-C_nH_{2n}-Si(OOCR^2)_3.$$

5. A compound of claim 1 of the formula $$R^1-Phe-Cy-O-C_nH_{2n}-Si(OOCR^2)_3.$$

6. A compound of claim 1 of the formula $$R^1-Cy-Cy-O-C_nH_{2n}-Si(OOCR^2)_3.$$

7. A compound of claim 1 wherein $R^1$ is alkyl or alkyl containing oxygen atoms.
8. A compound of claim 1 wherein n is 3.
9. A compound of claim 1 wherein $C_nH_{2n}$ is $-(CH_2)_n-$.
10. A compound of claim 1 wherein all alkyl portions are straight chained.
11. A compound of claim 1 wherein $R^2$ is methyl.
12. In a liquid-crystalline dielectric medium useful for visual electronic display elements, and having at least two liquid-crystalline components, the improvement wherein at least one component is a compound of claim 1.
13. A dielectric of claim 12 wherein the amount of said compound is 0.01-1 wt %.
14. In an electro-optical visual electronic display element, comprising a liquid crystalline dielectric, the improvement wherein the dielectric is one of claim 12.
15. A substrate useful in visual electronic display elements coated with a layer of a compound of claim 1.
16. A coated substrate of claim 15 which is a glass substrate.
17. In a method for generating a homeotropic orientation of a liquid crystalline phase in contact with a surface comprising employing at said surface a substrate coated with a layer which facilitates said homeotropic orientation, the improvement wherein the coated substrate is one of claim 16.
18. In an electro-optical visual electronic display element, comprising a liquid crystalline dielectric, and in contact therewith, a substrate coated with a layer which facilitates a homeotropic orientation in said dielectric, the improvement wherein the coated substrate is one of claim 16.
19. A compound of the formula $R^1-A^1-A^2-O-C_nH_{2n}-SiCl_3$ wherein $R^1$, is H, alkyl of 1-10 C atoms, alkyl of 1-10 C atoms wherein one or two nonadjacent $CH_2$ groups are replaced by oxygen atoms, F, Cl, Br or CN; $A^1$ and $A^2$ are independently each 1,4/phenylene (Phe) or 1,4-cyclohexylene (Cy); and n is 2, 3, 4, 5 or 6.

* * * * *